United States Patent
Kassab

(10) Patent No.: US 9,504,486 B2
(45) Date of Patent: *Nov. 29, 2016

(54) DEVICES, SYSTEMS, AND METHODS FOR VALVE REMOVAL

(71) Applicant: CVDevices, LLC, San Diego, CA (US)

(72) Inventor: Ghassan S. Kassab, La Jolla, CA (US)

(73) Assignee: CVDevices, LLC, San Diego, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 14/196,199

(22) Filed: Mar. 4, 2014

(65) Prior Publication Data

US 2014/0188125 A1    Jul. 3, 2014

Related U.S. Application Data

(63) Continuation of application No. 12/602,337, filed on Apr. 19, 2010, now Pat. No. 8,663,217.

(51) Int. Cl.
| | |
|---|---|
| *A61B 18/18* | (2006.01) |
| *A61B 17/3207* | (2006.01) |
| *A61B 17/221* | (2006.01) |
| *A61B 17/22* | (2006.01) |

(52) U.S. Cl.
CPC ..... *A61B 17/320758* (2013.01); *A61B 17/221* (2013.01); *A61B 17/32075* (2013.01); *A61B 17/320725* (2013.01); *A61B 2017/22097* (2013.01); *A61B 2017/22098* (2013.01); *A61B 2017/320716* (2013.01); *A61B 2017/320775* (2013.01)

(58) Field of Classification Search
CPC ............ A61B 2017/22097; A61B 17/320758; A61B 17/320725; A61B 17/221

USPC ............ 604/27, 508, 509; 623/1.26; 606/41, 606/159

See application file for complete search history.

(56) References Cited

U.S. PATENT DOCUMENTS

| | | | |
|---|---|---|---|
| 5,295,958 A | | 3/1994 | Shturman |
| 5,370,685 A | | 12/1994 | Stevens |
| 5,443,446 A | | 8/1995 | Shturman |
| 5,545,214 A | | 8/1996 | Stevens |
| 6,126,635 A | * | 10/2000 | Simpson ........ A61B 17/320758 604/101.05 |
| 6,338,735 B1 | | 1/2002 | Stevens |
| 6,540,761 B2 | * | 4/2003 | Houser .............. A61B 18/1492 606/170 |
| 6,830,584 B1 | * | 12/2004 | Seguin .................. A61F 2/2436 623/2.11 |
| 6,896,690 B1 | | 5/2005 | Lambrecht et al. |

(Continued)

OTHER PUBLICATIONS

International Searching Authority, International Search report, mailed Oct. 2, 2008 (PCT/US08/64974).
International Searching Authority, Written Opinion of the International Searching Authority, mailed Oct. 2, 2008 (PCT/US08/64974).

*Primary Examiner* — Jocelyn D Ram
(74) *Attorney, Agent, or Firm* — Reichel Stohry LLP; Mark C. Reichel; Natalie J. Dean

(57) ABSTRACT

Devices, systems, and methods for valve removal. In an embodiment of an umbrella device for removing a valve of the present disclosure, the umbrella device comprises an elongated shaft having a distal end, a first umbrella comprising a first mesh, the first umbrella coupled to the shaft at or near the distal end of the shaft, a second umbrella comprising a second mesh, the second umbrella coupled to the shaft proximal to the first umbrella, and a mechanical drill rotatably coupled to the shaft and positioned between the first umbrella and the second umbrella.

20 Claims, 10 Drawing Sheets

(56) References Cited

U.S. PATENT DOCUMENTS

| | | | |
|---|---|---|---|
| 6,989,027 B2* | 1/2006 | Allen | A61F 2/2412 606/200 |
| 7,255,706 B2 | 8/2007 | Rosengart | |
| 7,815,676 B2 | 10/2010 | Greenberg | |
| 8,016,877 B2* | 9/2011 | Seguin | A61F 2/2412 623/1.24 |
| 8,372,069 B2 | 2/2013 | Kassab | |
| 2002/0058995 A1 | 5/2002 | Stevens | |
| 2004/0236418 A1 | 11/2004 | Stevens | |
| 2005/0015112 A1 | 1/2005 | Cohn et al. | |
| 2005/0096647 A1 | 5/2005 | Steinke et al. | |
| 2005/0131438 A1* | 6/2005 | Cohn | A61F 2/2427 606/170 |
| 2005/0203570 A1 | 9/2005 | Mazzocchi et al. | |
| 2005/0240200 A1 | 10/2005 | Bergheim | |
| 2006/0074485 A1 | 4/2006 | Realyvasquez | |
| 2006/0199995 A1* | 9/2006 | Vijay | A61B 17/12022 600/37 |
| 2007/0021774 A1 | 1/2007 | Hogendijk | |
| 2007/0027534 A1* | 2/2007 | Bergheim | A61F 2/013 623/2.11 |
| 2007/0043435 A1* | 2/2007 | Seguin | A61F 2/2418 623/2.11 |
| 2007/0185513 A1* | 8/2007 | Woolfson | A61F 2/2427 606/108 |
| 2007/0244552 A1 | 10/2007 | Salahieh et al. | |
| 2008/0039881 A1* | 2/2008 | Greenberg | A61B 17/22 606/170 |
| 2012/0172920 A1* | 7/2012 | Fifer | A61F 2/013 606/200 |

* cited by examiner

DEVICES, SYSTEMS, AND METHODS FOR VALVE REMOVAL

PRIORITY

This U.S. continuation patent application is related to, and claims the priority benefit of, U.S. patent application Ser. No. 12/602,337, filed Apr. 19, 2010 and issued as U.S. Pat. No. 8,663,217 on Mar. 4, 2014, which is related to, claims the priority benefit of, and is a U.S. national stage application of, International Patent Application No. PCT/US2008/064974, filed May 28, 2008, which is related to, and claims the priority benefit of, U.S. Provisional Patent Application Ser. No. 60/940,617, filed May 29, 2007. The contents of each of these applications are hereby incorporated by reference in their entirety into this disclosure.

BACKGROUND

The disclosure of the present application relates generally to tissue removal, and more particularly to devices, systems, and methods for percutaneous and mini-invasive valve removal.

For decades, percutaneous interventional therapy has been an option for patients with pulmolic, mitral, and/or aortic valvular disease. The treatment preferred in selected patients with pulmolic or mitral stenosis is percutaneous valvuloplasty. According to the current ACC/American Heart Association (AHA) guidelines in patients with calcific aortic stenosis, balloon aortic valvuloplasty (BAV) has been used as a bridge to aortic valve replacement.

Hospital mortality for BAV varies from 3.5% to 13.5%, while serious complications appear in at least 25% of the patients. The durability of BAV is restricted. Consequently, open aortic valve replacement continues to be the best therapy for aortic stenosis in patients who are viable candidates for surgery. The most frequent heart valve operation is the aortic valve replacement. In the United States, from 2% to 7% of individuals older than 65 years suffer from aortic stenosis (AS). The percentage of people over 65 years with aortic stenosis will continue to increase because people are living increasingly longer lives. Aortic stenosis is frequently associated with comorbid risk factors and previous bypass surgery because it is persistent and progressive and occurs frequently in elderly patients. The surgical therapy for AS patients is useful to improve symptoms and prolong life.

Percutaneous strategies for the treatment of AS began with percutaneous balloon valvuloplasty. Percutaneous balloon valvuloplasty data from the multicenter National Heart, Lung, and Blood Institute (NHLBI) registry shows only mild progress in early hemodynamics, a significant incidence of peripheral vascular complications, a 30-day mortality rate of 7%, and a high incidence of restenosis within 6 months.

Unsatisfactory results of balloon aortic valvuloplasty (BAV) have led to investigation of percutaneous placement of prosthetic aortic valves. Such devices are being clinically utilized in a small number of cases of high-risk patients. Although percutaneous aortic valve insertion has been performed on extremely high-risk patients, considerable paravalvular leak regurgitation and early mortality have discouraged this approach.

One of the biggest problems with percutaneous or transapical aortic valve replacement is the dilatation of a calcific aortic valve prior to delivery of the stent valve device. The consequences of irregular dilation of the aortic valve area are periprosthetic leak, calcium embolization, difficulties with device insertion and possible migration of the device.

In order to address these issues, present application discloses a device, system, and method for endovascular resection of the calcific aortic valve having the following features: a valve isolation system, a mechanism to cut and destroy a heavily calcified valve, and a technique and device to prevent migration or embolization of calcific debris into visceral organs. This device will set the stage for better delivery and insertion of the stent valve device.

BRIEF SUMMARY

In at least one embodiment of an umbrella device for removing a valve of the present disclosure, the umbrella device comprises a shaft catheter having a distal end and a proximal end, a first umbrella comprising a mesh, the first umbrella coupled to the shaft catheter at or near the distal end of the shaft catheter, a second umbrella comprising a mesh, the second umbrella coupled to the shaft catheter at or near the distal end of the shaft catheter, wherein the second umbrella is positioned along the shaft catheter proximally to the first umbrella, and a mechanical drill comprising at least one blade, the mechanical drill rotatably coupled to the shaft catheter and positioned between the first umbrella and the second umbrella, wherein the umbrella device is operable to be introduced into a vessel, engage a valve, and remove said valve. In another embodiment, the shaft catheter comprises a wall defining a lumen positioned therethrough. In yet another embodiment, the umbrella device further comprises a wire positioned within at least part of the lumen of the shaft catheter, the wire operable to position a temporary stent valve within the vessel. In an additional embodiment, the wire is further operable to position a permanent stent valve within the vessel. In yet an additional embodiment, the first umbrella and the second umbrella are capable of mechanical expansion and contraction.

In at least one embodiment of an umbrella device for removing a valve of the present disclosure, the first umbrella and the second umbrella are capable of electromechanical expansion and contraction. In another embodiment, the umbrella device further comprises electrical coils positioned along portions of the shaft catheter at or near the first umbrella and the second umbrella, wherein the electrical coils are operable to generate a magnetic force upon introduction of a current to said electrical coils. In yet another embodiment, the current is introduced from a current source, the current source operably coupled to the electrical coils. In an additional embodiment, the mesh of the first umbrella and the second umbrella defines mesh apertures no larger than 100 µm in diameter. In yet an additional embodiment, the mesh of the first umbrella and the second umbrella defines mesh apertures between 10 µm and 100 µm in diameter.

In at least one embodiment of an umbrella device for removing a valve of the present disclosure, the mesh comprises mesh material selected from the group consisting of stainless steel, microexpandable metal, polytetrafluoroethylene coated stainless steel, and polyethylene terephthalate coated stainless steel. In another embodiment, the mesh of the first umbrella and the second umbrella defines mesh apertures having a diameter large enough to allow blood to pass therethrough but small enough to prevent ground valve from passing therethrough. In yet another embodiment, the first umbrella comprises a cauterizing mechanism coupled to a circumferential edge of the first umbrella. In an additional embodiment, the cauterizing mechanism comprises a cauterizing wire capable of increasing in temperature from the introduction of a current to said cauterizing wire. In yet an additional embodiment, the second umbrella comprises a cauterizing mechanism coupled to a circumferential edge of the second umbrella.

In at least one embodiment of an umbrella device for removing a valve of the present disclosure, the cauterizing mechanism comprises a cauterizing wire capable of increasing in temperature from the introduction of a current to said cauterizing wire. In another embodiment, the first umbrella comprises a first cauterizing mechanism coupled to a circumferential edge of the first umbrella and a second cauterizing mechanism coupled to a circumferential edge of the second umbrella, wherein the cauterizing mechanism comprises cauterizing wires capable of increasing in temperature from the introduction of a current to said cauterizing wires. In yet another embodiment, the cauterizing mechanism is operable to cauterize the valve to detach the valve from the vessel. In an additional embodiment, the mechanical drill is operable via operation of an electrical source coupled thereto, the electrical source operable to start and stop rotation of the at least one blade of the mechanical drill. In yet an additional embodiment, the mechanical drill is operable via operation of a suction source coupled thereto, the suction source operable to start and stop rotation of the at least one blade of the mechanical drill.

In at least one embodiment of a method for removing a valve from a vessel according to the present disclosure, the method comprises the steps of introducing an umbrella device into a vessel, the umbrella device comprising a shaft catheter having a distal end and a proximal end, a first umbrella comprising a mesh, the first umbrella coupled to the shaft catheter at or near the distal end of the shaft catheter, a second umbrella comprising a mesh, the second umbrella coupled to the shaft catheter at or near the distal end of the shaft catheter, wherein the second umbrella is positioned along the shaft catheter proximally to the first umbrella, and a mechanical drill comprising at least one blade, the mechanical drill rotatably coupled to the shaft catheter and positioned between the first umbrella and the second umbrella, positioning the umbrella device within an aperture within the valve, deploying the first umbrella on a first side of the valve, wherein the deployed first umbrella engages the valve at the first side of the valve, deploying the second umbrella on a second side of the valve, wherein the deployed second umbrella engages the valve at the second side of the valve, operating the mechanical drill to grind the valve, collapsing the first umbrella and the second umbrella to facilitate withdrawal of the umbrella device from the vessel, and withdrawing the umbrella device from the vessel. In another embodiment, the first umbrella comprises a first cauterizing mechanism coupled to a circumferential edge of the first umbrella, and the method further comprises the step of cauterizing the valve using the first cauterizing mechanism to excise the valve from the vessel prior to the step of operating the mechanical drill to grind the valve. In yet another embodiment, the second umbrella comprises a second cauterizing mechanism coupled to a circumferential edge of the second umbrella, and the method further comprises the step of cauterizing the valve using the second cauterizing mechanism to excise the valve from the vessel prior to the step of operating the mechanical drill to grind the valve. In an additional embodiment, the first umbrella comprises a first cauterizing mechanism coupled to a circumferential edge of the first umbrella, and wherein the second umbrella comprises a second cauterizing mechanism coupled to a circumferential edge of the second umbrella, and the method further comprises the step of cauterizing the valve using the first cauterizing mechanism and the second cauterizing mechanism simultaneously to excise the valve from the vessel prior to the step of operating the mechanical drill to grind the valve. In yet an additional embodiment, the method further comprises the step of positioning a temporary stent valve within the vessel using the umbrella device prior to the step of positioning the umbrella device within an aperture within the valve.

In at least one embodiment of a method for removing a valve from a vessel according to the present disclosure, the method further comprises the step of positioning a permanent stent valve at or near the position of the excised valve. In another embodiment, the method further comprises the step of removing the temporary stent valve from the vessel.

In at least one embodiment of a method for removing a valve from a vessel according to the present disclosure, the method comprising the steps of introducing an first apparatus into a vessel to position a temporary stent valve, positioning a temporary stent valve within the vessel using the first apparatus, introducing an umbrella device within the vessel to excise a vessel valve, positioning the umbrella device within an aperture within the valve, excising the valve using the umbrella device, withdrawing the umbrella device with the excised valve contained therein from the vessel, introducing a second apparatus into a vessel to position a permanent stent valve, positioning a permanent stent valve at or near the position of the excised valve using the second apparatus, and withdrawing the second apparatus from the vessel. In another embodiment, the first apparatus and the second apparatus comprise a catheter. In yet another embodiment, the catheter comprises a wall defining a lumen positioned therethrough. In an additional embodiment, the catheter further comprises a wire positioned within at least part of the lumen of the catheter, wherein the wire is operable to position the temporary stent valve or the permanent stent valve within the vessel. In yet an additional embodiment, the first apparatus and the second apparatus comprise the same apparatus.

In at least one embodiment of a method for removing a valve from a vessel according to the present disclosure, the first apparatus and the second apparatus comprise an umbrella device. In another embodiment, wherein the umbrella device comprises a shaft catheter having a distal end and a proximal end, a first umbrella comprising a mesh and a first cauterizing mechanism coupled to a circumferential edge of the first umbrella, the first umbrella coupled to the shaft catheter at or near the distal end of the shaft catheter, a second umbrella comprising a mesh and a second cauterizing mechanism coupled to a circumferential edge of the second umbrella, the second umbrella coupled to the shaft catheter at or near the distal end of the shaft catheter, wherein the second umbrella is positioned along the shaft catheter proximally to the first umbrella, and a mechanical drill comprising at least one blade, the mechanical drill rotatably coupled to the shaft catheter and positioned between the first umbrella and the second umbrella. In yet another embodiment, the step of positioning the umbrella device within an aperture within the valve comprises the step of deploying the first umbrella on a first side of the valve, wherein the deployed first umbrella engages the valve at the first side of the valve, and further comprises the step of deploying the second umbrella on a second side of the valve, wherein the deployed second umbrella engages the valve at the second side of the valve. In an additional embodiment, the step of excising the valve using the umbrella device comprises the step of cauterizing the valve using the first cauterizing mechanism and the second cauterizing mechanism simultaneously to excise the valve, and further comprises the step of operating the mechanical drill to grind the valve. In yet an additional embodiment, the method further comprising the step of removing the temporary stent valve from the vessel.

In at least one embodiment of a method for removing a valve from a vessel according to the present disclosure, the step of removing the temporary stent valve is performed using the second apparatus. In another embodiment, the step of removing the temporary stent valve is performed using the umbrella device.

In at least one embodiment of a method for removing a valve from a vessel according to the present disclosure, the method comprises the steps of introducing an umbrella device into a vessel, the umbrella device comprising a first umbrella comprising a mesh and a first cauterizing mechanism coupled to a circumferential edge of the first umbrella, the first umbrella coupled to the shaft catheter at or near the distal end of the shaft catheter, a second umbrella comprising a mesh and a second cauterizing mechanism coupled to a circumferential edge of the second umbrella, the second umbrella coupled to the shaft catheter at or near the distal end of the shaft catheter, wherein the second umbrella is positioned along the shaft catheter proximally to the first umbrella, and a mechanical drill comprising at least one blade, the mechanical drill rotatably coupled to the shaft catheter and positioned between the first umbrella and the second umbrella, positioning a temporary stent valve within the vessel, positioning the umbrella device within an aperture within the valve, deploying the first umbrella on a first side of the valve, wherein the deployed first umbrella engages the valve at the first side of the valve, deploying the second umbrella on a second side of the valve, wherein the deployed second umbrella engages the valve at the second side of the valve, cauterizing the valve using the first cauterizing mechanism and the second cauterizing mechanism to excise the valve from the vessel, operating the mechanical drill to grind the excised valve, collapsing the first umbrella and the second umbrella to facilitate withdrawal of the umbrella device containing the excised valve from the vessel, withdrawing the umbrella device containing the excised valve from the vessel, positioning a permanent stent valve at or near the position of the excised valve, and removing the temporary stent valve from the vessel. In another embodiment, the step of positioning a temporary stent valve within the vessel is performed using a catheter. In yet another embodiment, the step of positioning a temporary stent valve within the vessel is performed using the umbrella device. In an additional embodiment, the step of positioning a permanent stent valve at or near the position of the excised valve is performed using a catheter. In yet an additional embodiment, the step of positioning a permanent stent valve at or near the position of the excised valve is performed using the umbrella device.

In at least one embodiment of a method for removing a valve from a vessel according to the present disclosure, the step of removing the temporary stent valve from the vessel is performed using a catheter. In another embodiment, the step of removing the temporary stent valve from the vessel is performed using the umbrella device.

In at least one embodiment of a system for removing a valve from a vessel according to the present disclosure, the system comprises an umbrella device comprising a shaft catheter having a distal end and a proximal end, a first umbrella comprising a mesh, the first umbrella coupled to the shaft catheter at or near the distal end of the shaft catheter, a second umbrella comprising a mesh, the second umbrella coupled to the shaft catheter at or near the distal end of the shaft catheter, wherein the second umbrella is positioned along the shaft catheter proximally to the first umbrella, and a mechanical drill comprising at least one blade, the mechanical drill rotatably coupled to the shaft catheter and positioned between the first umbrella and the second umbrella, and at least one mechanism capable of expanding and contracting the first umbrella and the second umbrella, wherein the umbrella device is operable to be introduced into a vessel, engage a valve, and remove said valve. In another embodiment, the first umbrella and the second umbrella are capable of mechanical expansion and contraction. In yet another embodiment, the first umbrella and the second umbrella are capable of electromechanical expansion and contraction. In an additional embodiment, the at least one mechanism comprises at least one mechanical mechanism operable to mechanically expand and contract the first umbrella and the second umbrella. In yet an additional embodiment, the at least one mechanical mechanism comprises at least one rib slidingly coupled to the shaft catheter, wherein the at least one rib may be moved along the shaft catheter toward the distal end and toward the proximal end to mechanically expand and contract the first umbrella and the second umbrella.

In at least one embodiment of a system for removing a valve from a vessel according to the present disclosure, the at least one mechanism comprises at least one electromechanical mechanism operable to electromechanically expand and contract the first umbrella and the second umbrella. In another embodiment, the at least one electromechanical mechanism comprises electrical coils positioned along portions of the shaft catheter at or near the first umbrella and the second umbrella, wherein the electrical coils are operable to generate a magnetic force upon introduction of a current to said electrical coils. In yet another embodiment, the current is introduced from a current source, the current source operably coupled to the electrical coils. In an additional embodiment, the shaft catheter comprises a wall defining a lumen positioned therethrough. In yet an additional embodiment, the system further comprises a wire positioned within at least part of the lumen of the shaft catheter, the wire operable to position a temporary stent valve within the vessel.

In at least one embodiment of a system for removing a valve from a vessel according to the present disclosure, the wire is further operable to position a permanent stent valve within the vessel. In another embodiment, the mesh of the first umbrella and the second umbrella defines mesh apertures no larger than 100 µm in diameter. In yet another embodiment, the mesh comprises mesh material selected from the group consisting of stainless steel, microexpandable metal, polytetrafluoroethylene coated stainless steel, and polyethylene terephthalate coated stainless steel. In an additional embodiment, the mesh of the first umbrella and the second umbrella defines mesh apertures having a diameter large enough to allow blood to pass therethrough but small enough to prevent ground valve from passing therethrough. In yet an additional embodiment, the first umbrella comprises a cauterizing mechanism coupled to a circumferential edge of the first umbrella.

In at least one embodiment of a system for removing a valve from a vessel according to the present disclosure, the cauterizing mechanism comprises a cauterizing wire capable of increasing in temperature from the introduction of a current to said cauterizing wire. In another embodiment, the second umbrella comprises a cauterizing mechanism coupled to a circumferential edge of the second umbrella. In yet another embodiment, the cauterizing mechanism comprises a cauterizing wire capable of increasing in temperature from the introduction of a current to said cauterizing wire. In an additional embodiment, the first umbrella comprises a first cauterizing mechanism coupled to a circumferential edge of the first umbrella and a second cauterizing mechanism coupled to a circumferential edge of the second umbrella, wherein the cauterizing mechanisms comprises cauterizing wires capable of increasing in temperature from the introduction of a current to said cauterizing wires. In yet an additional embodiment, the cauterizing mechanism is operable to cauterize the valve to detach the valve from the vessel.

In at least one embodiment of a system for removing a valve from a vessel according to the present disclosure, the cauterizing mechanism is operable to cauterize the valve to detach the valve from the vessel. In another embodiment, the mechanical drill is operable via operation of an electrical source coupled thereto, the electrical source operable to start and stop rotation of the at least one blade of the mechanical drill. In yet another embodiment, the mechanical drill is operable via operation of a suction source coupled thereto, the suction source operable to start and stop rotation of the at least one blade of the mechanical drill.

DETAILED DESCRIPTION

Figure 1:
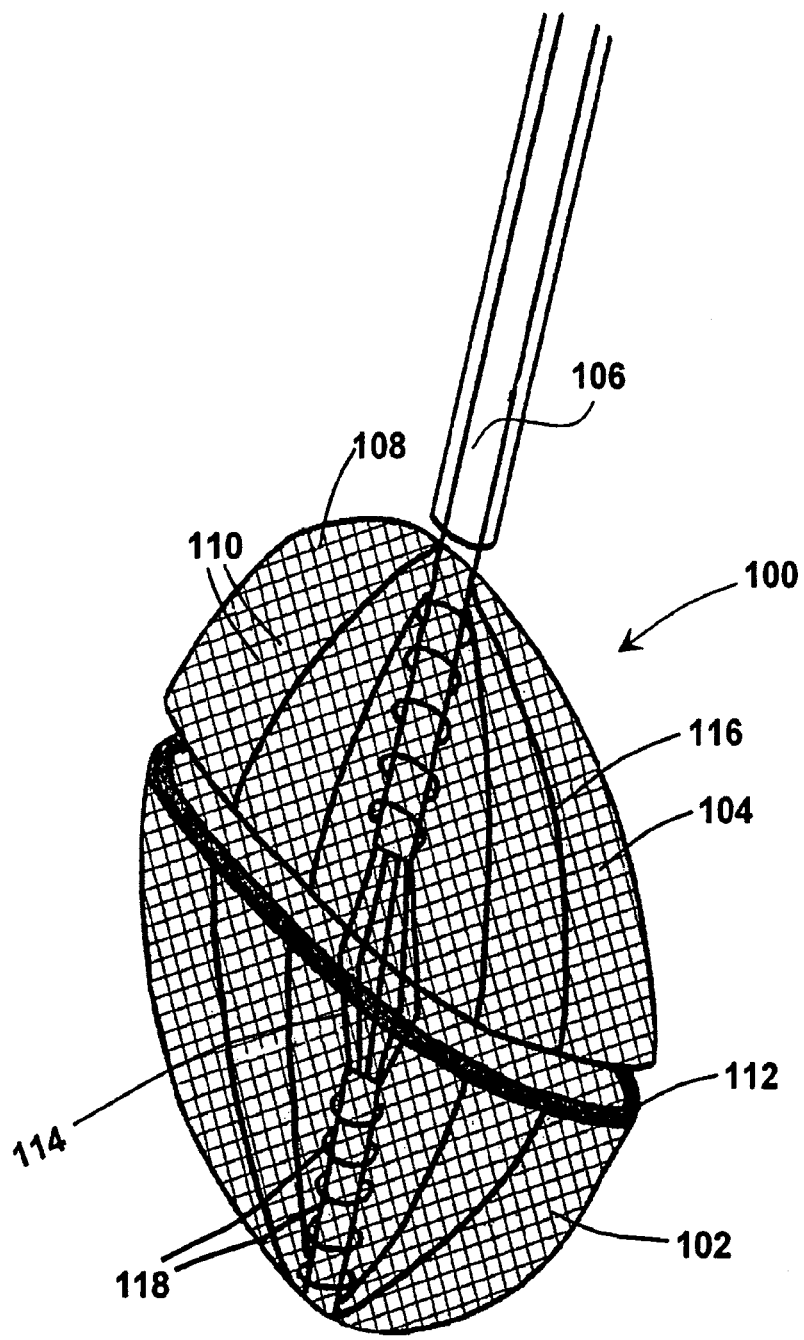
FIG. 1 shows an umbrella device according to at least one embodiment of the present application, as described herein.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application relates generally to tissue removal, and more particularly to devices, systems, and methods for percutaneous and mini-invasive valve removal. In at least one embodiment, an umbrella device comprises two opposing umbrellas, a cauterizing mechanism, and a drill, wherein the umbrella device is operable to percutaneously engage and remove a valve.

An exemplary embodiment of an umbrella device according to the present disclosure is shown in FIG. 1. As shown in FIG. 1, umbrella device 100 comprises a first umbrella 102 and a second umbrella 104 coupled to shaft catheter 106. As shown in the exemplary embodiment of umbrella device 100 in FIG. 1, umbrella device 100 comprises fully deployed (or expanded) first umbrella 102 and second umbrella 104.

Figure 10B:
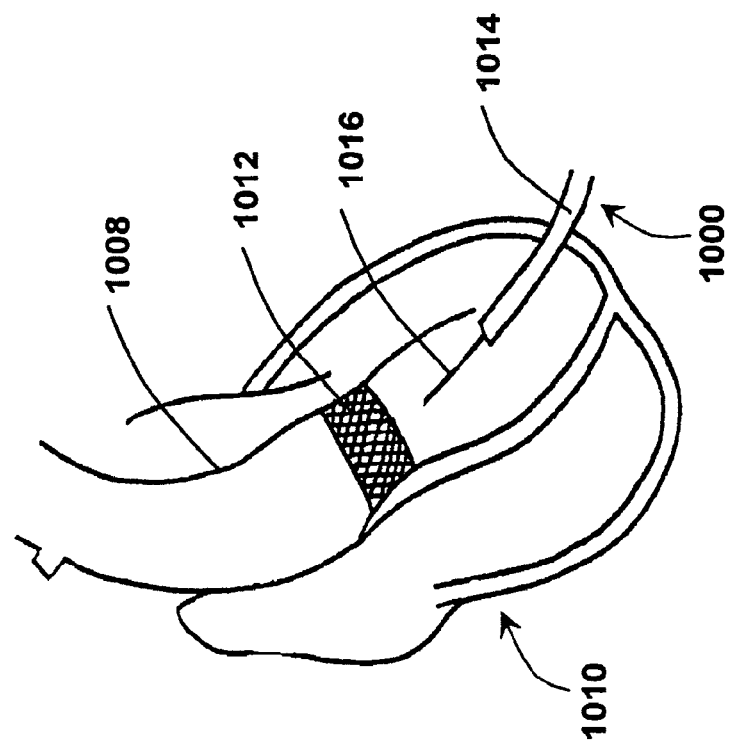
FIG. 10B shows an umbrella device according to at least one embodiment of the present application useful for positioning a permanent stent valve, as described herein.

Shaft catheter 106 may comprise a distal end and a proximal end, and may further comprise a wall defining a lumen therethrough. In at least one embodiment, shaft catheter may comprise a wire 1016 (as shown in FIG. 10B), wherein wire 1016 may be useful to position one or more stents within a vessel as described herein.

First umbrella 102 and second umbrella 104 comprise a mesh 108 defining apertures 110, wherein the mesh 108 is capable of holding particulates (as described in greater detail herein) as desired for a particular application. Mesh 108 may comprise, but is not limited to, stainless steel wire mesh, microexpanded metal, polytetrafluoroethylene (PTFE) or polyethylene terephthalate ("PETE," or Dacron, for example) reinforced with stainless steel wire mesh, and/or any number of other substances suitable for comprising mesh 108. In at least one embodiment, mesh 108 defines apertures no larger than 100 μm in diameter, noting that the diameter of a red blood cell is approximately 7 μm. In at least one embodiment, mesh 108 defines apertures large enough to allow blood to pass therethrough but small enough to prevent, for example, ground calcified aortic valve as described herein, from passing therethrough.

As shown in FIG. 1, first umbrella 102 and second umbrella 104 are positioned along shaft catheter 106 so that when first umbrella 102 and second umbrella 104 are deployed or expanded, the open ends of first umbrella 102 and second umbrella 104 face one another. In other words, when first umbrella 102 and second umbrella 104 are expanded, the circumferential edges of expanded first umbrella 102 and second umbrella 104, if approaching or in contact with one another, would form an enclosure (or chamber) as shown in FIG. 1.

First umbrella 102 and/or second umbrella 104 may further comprise a cauterizing mechanism 112 positioned along the circumferential edge of first umbrella 102 and/or second umbrella 104. As shown in FIG. 1, first umbrella 102 comprises cauterizing mechanism 112, wherein cauterizing mechanism 112 is operable to remove all or part of, for example, a calcified aortic valve as described in further detail herein. Cauterizing mechanism 112 may comprise, for example, a cauterizing wire that may be heated via introduction of a current source to said wire.

First umbrella 102 and/or second umbrella 104 may be collapsed and/or expanded mechanically, as with a commonly-known umbrella, or electromagnetically, as shown in the exemplary embodiment of umbrella device 100 shown in FIG. 1. In an embodiment of a first umbrella 102 and/or second umbrella 104 capable of mechanical expansion, a mechanism (for example, a rib 116 slidingly engaged to shaft catheter 106), may be moved along shaft catheter 106 to facilitate expansion and contraction of first umbrella 102 and/or second umbrella 104. As shown in the exemplary embodiment of umbrella device 100 shown in FIG. 1, umbrella device comprises electrical coils 118 surrounding portions of shaft catheter 106. Electrical coils 118, when used to electromagnetically collapse and/or expand first umbrella 102 and/or second umbrella 104, generate a magnetic force which can either repel first umbrella 102 and/or second umbrella 104 to open the umbrellas or attract first umbrella 102 and/or second umbrella 104 to close the umbrellas. In such an embodiment, a current source (not shown) would be coupled to electrical coils 118 so that currents of varying polarities could be introduced to expand and/or collapse first umbrella 102 and/or second umbrella 104 as desired.

Figure 2A:
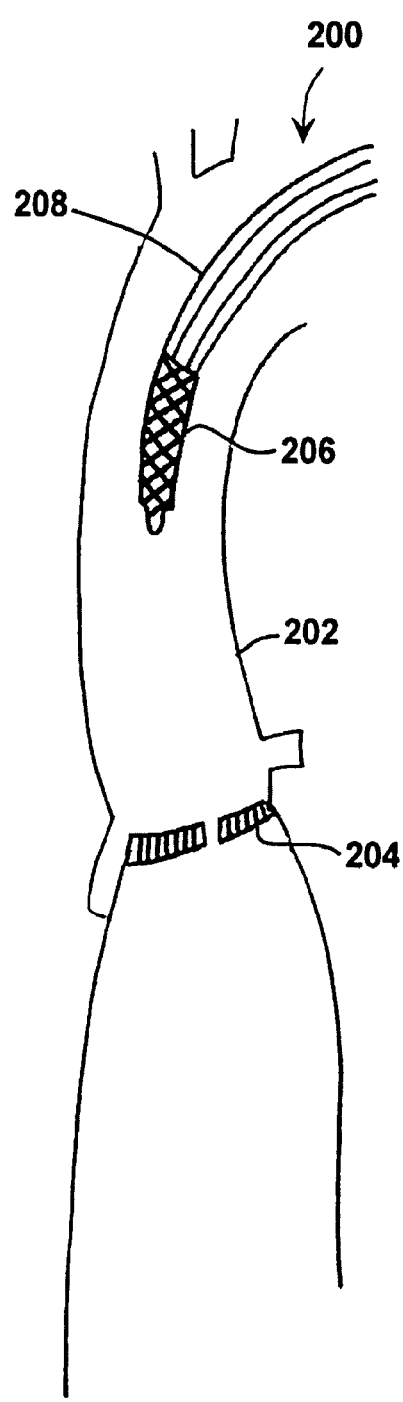
FIG. 2A shows an umbrella device according to at least one embodiment of the present application positioning a temporary stent valve within a vessel, as described herein.
Figure 2B:
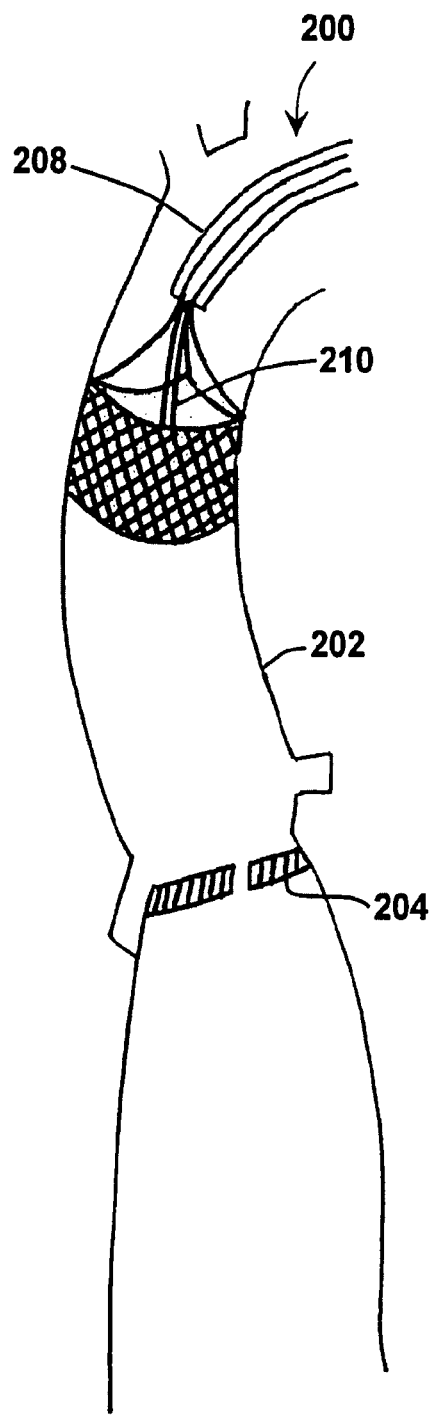
FIG. 2B shows an umbrella device according to at least one embodiment of the present application with a temporary stent valve positioned within a vessel, as described herein.

As shown in the exemplary embodiment of umbrella device 100 in FIG. 1, umbrella device 100 further comprises a miniature drill 114. Drill 114 may comprise one or more blades operable to grind, for example, a calcified aortic valve, as described in further detail herein. Drill 114 may allow for the pulverization of the calcific calcium material at the level of the aortic leaflet, with the pulverized material removed by umbrella device 100 as described herein. Drill 114 may be electrically operable via operation of a current source (not shown) coupled thereto, or drill 114 may be operable using suction, whereby suction operates to turn blades of drill 114 to allow for cutting as described herein. It can be appreciated that any number of miniature drills known or anticipated in the art may be useful with the disclosure of the present application, An exemplary embodiment of an umbrella device positioning a temporary stent valve within a vessel is shown in FIGS. 2A and 2B. As shown in FIGS. 2A and 2B, umbrella device 200 is shown introduced into a lumen of a vessel 202 proximal to, for example, a calcified aortic valve 204. During such an endovascular procedure, when umbrella device 200 is positioned at a desired location within vessel 202, umbrella device 200 may deliver a temporary stent valve 206. As shown in FIG. 2A, temporary stent valve 206 is positioned at or near the proximal end of shaft catheter 208 of umbrella device 200, and is shown in a collapsed configuration. It can be appreciated that in at least one embodiment of the present disclosure, umbrella device 200 may be useful for the excision of a valve as described herein, but a second apparatus, for example a catheter with a wire, may be useful for the placement of temporary stent valve 206.

When temporary stent valve 206 is positioned at a desired location within vessel 202, umbrella device 200 may place temporary stent valve 206 within vessel 202 as shown in FIG. 2B. As shown in FIG. 2B, temporary stent valve 206 is shown in a deployed (or expanded) configuration. Temporary stent valve 206 may comprise a stitch 210 useful for collapsing and/or expanding temporary stent valve 206. Temporary stent valve 206 may be useful to prevent backflow of blood in a similar fashion to a native heart valve, allowing a user of an umbrella device of the present application to perform the procedures described herein without compromising natural heart function. Temporary stent valve 206 may be flexible and may comprise polyurethane or another biologically-compatible material. It can be appreciated that any number of temporary stent valves 206 known or anticipated in the art may be useful with the disclosure of the present application.

Figure 3A:
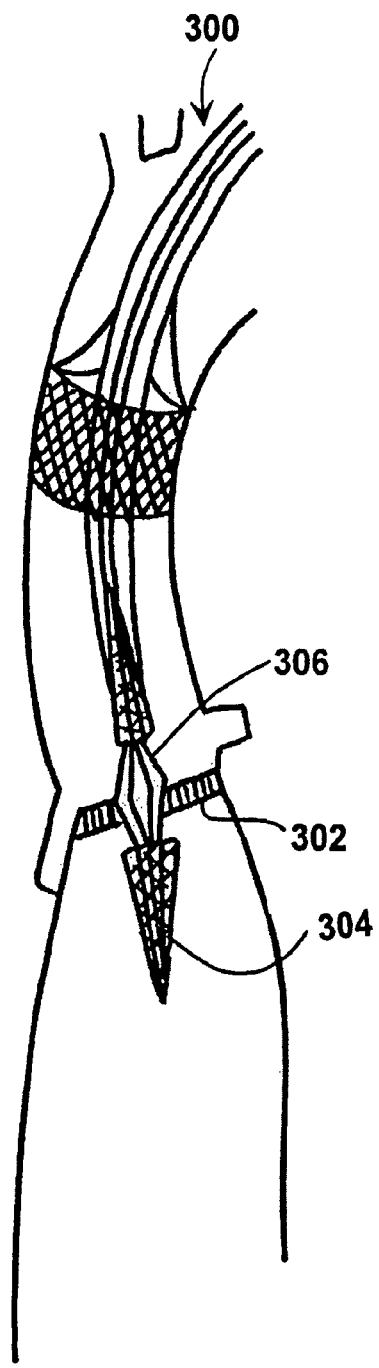
FIG. 3A shows an umbrella device according to at least one embodiment of the present application positioning a first umbrella at an aortic valve site within a vessel, as described herein.
Figure 3B:
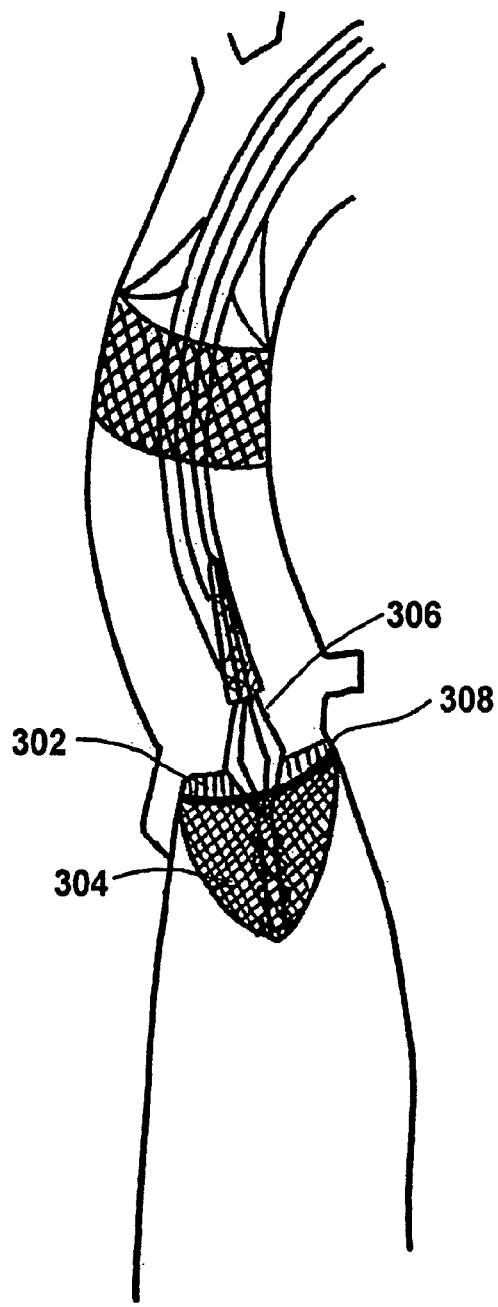
FIG. 3B shows an umbrella device according to at least one embodiment of the present application with the first umbrella positioned at an aortic valve site within a vessel, as described herein.

FIGS. 3A and 3B show an embodiment of an umbrella device within a vessel at or near a calcified aortic valve. As shown in FIG. 3A, a portion of umbrella device 300 is shown positioned within calcified aortic valve 302, whereby first umbrella 304 is inferiorally positioned after calcified aortic valve 302. Drill 306 of umbrella device 300 is shown in FIGS. 3A and 3B at or near calcified aortic valve 302 so that drill 306, when in operation, may operate to grind calcified aortic valve 302 as discussed herein.

When first umbrella 304 of umbrella device 300 is positioned inferiorally after calcified aortic valve 302, first umbrella may be expanded (or deployed) as shown in FIG. 3B. As shown in FIG. 3B, when first umbrella 304 is expanded, the outer circumference of first umbrella 304 may engage calcified aortic valve 302, whereby operation of a cauterizing mechanism 308 positioned at or near the circumferential edge of expanded first umbrella 304 may be useful to cauterize calcified aortic valve 302 to allow for subsequent grinding by drill 306 as described herein. It can be appreciated that in various embodiments of an umbrella device as described herein, a cauterizing mechanism may be positioned at or near the circumferential edge of a first umbrella and/or a second umbrella, recognizing that positioning a cauterizing mechanism on one umbrella would allow cauterization from one direction while positioning a cauterizing mechanism on both umbrellas would allow cauterization from both directions.

Figure 4A:
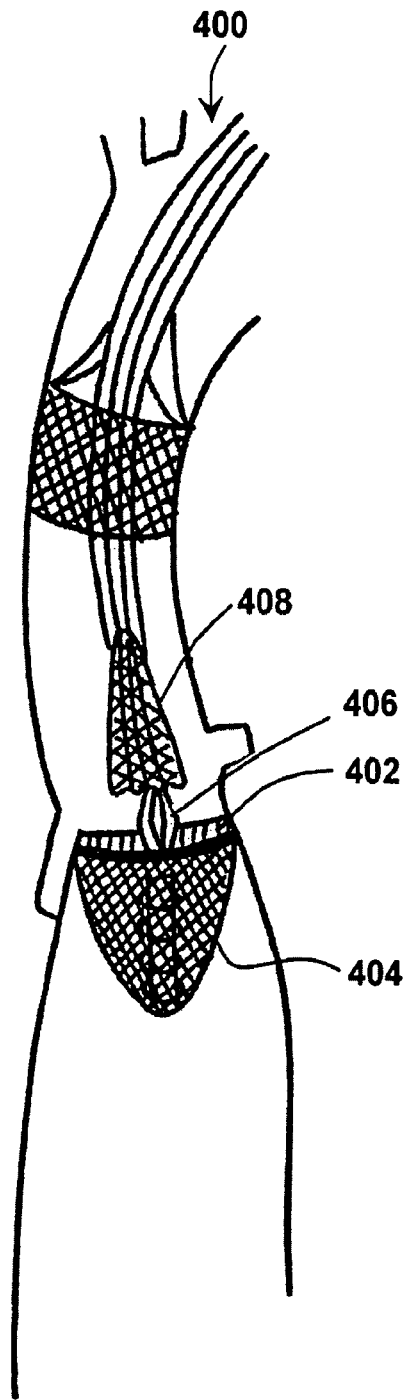
FIG. 4A shows an umbrella device according to at least one embodiment of the present application positioning a second umbrella at an aortic valve site within a vessel, as described herein.
Figure 4B:
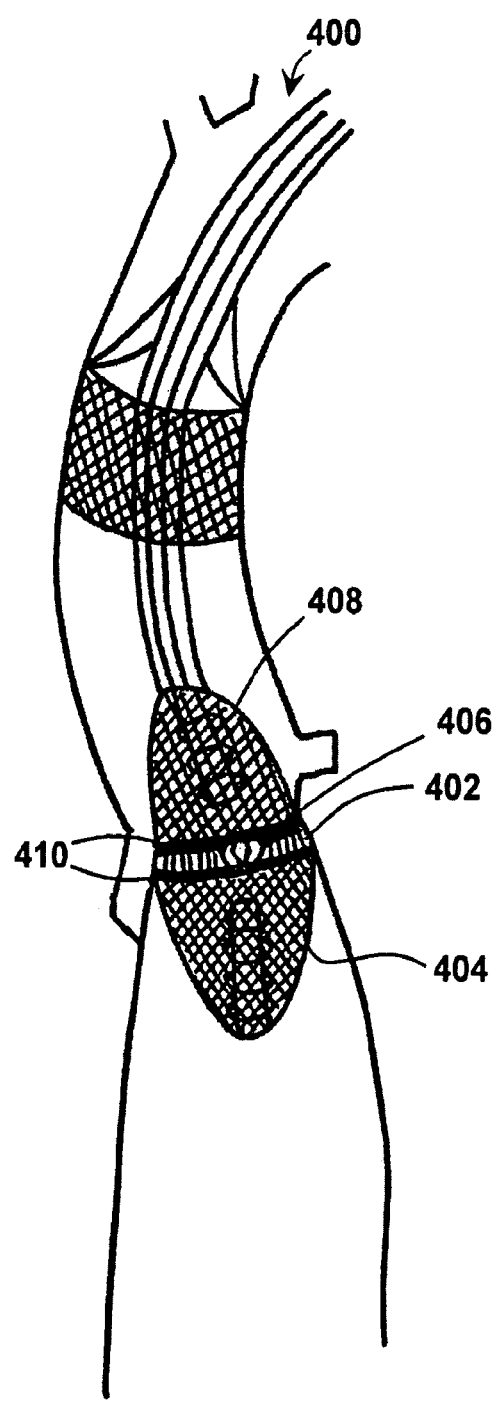
FIG. 4B shows an umbrella device according to at least one embodiment of the present application with the second umbrella positioned at an aortic valve site within a vessel, as described herein.

FIGS. 4A and 4B show an embodiment of an umbrella device within a vessel with a deployed first umbrella and a deploying second umbrella at or near a calcified aortic valve. As shown in FIGS. 4A and 4B, a portion of umbrella device 400 is shown positioned within calcified aortic valve 402, whereby first umbrella 404 is inferiorally positioned and expanded after calcified aortic valve 402. Drill 406 of umbrella device 400 is shown in FIGS. 4A and 4B at or near calcified aortic valve 402 so that drill 406, when in operation, may operate to grind calcified aortic valve 402 as discussed herein.

As shown in FIG. 4A, second umbrella 408 is superiorially positioned before calcified aortic valve 402, and second umbrella 408 has started to expand. FIG. 4B shows an exemplary embodiment of umbrella device 400 with a fully expanded second umbrella 408. As shown in FIG. 4B, when first umbrella 404 and second umbrella 408 are expanded, the outer circumferences of first umbrella 404 and second umbrella 408 may engage calcified aortic valve 402 from both sides, whereby operation of a cauterizing mechanism 410 of either or both first umbrella 404 and/or second umbrella 408 positioned at or near the circumferential edges of either or both expanded first umbrella 404 and/or second umbrella 408 may be useful to cauterize calcified aortic valve 402 to allow for subsequent grinding by drill 406 as described herein. As shown in the exemplary embodiment of FIG. 4B, first umbrella 404 and second umbrella 408 each have a cauterizing mechanism 410 positioned thereon.

Figure 5C:
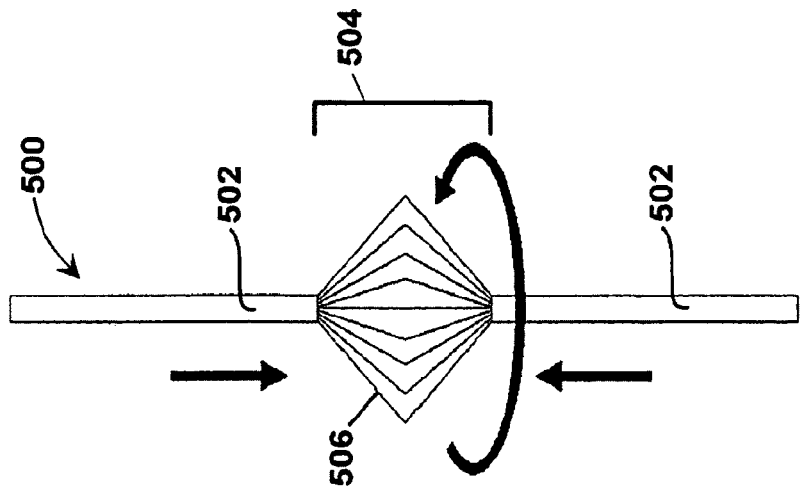
FIG. 5C shows a drill of an umbrella device according to at least one embodiment of the present application operably rotating, as described herein.
Figure 5B:
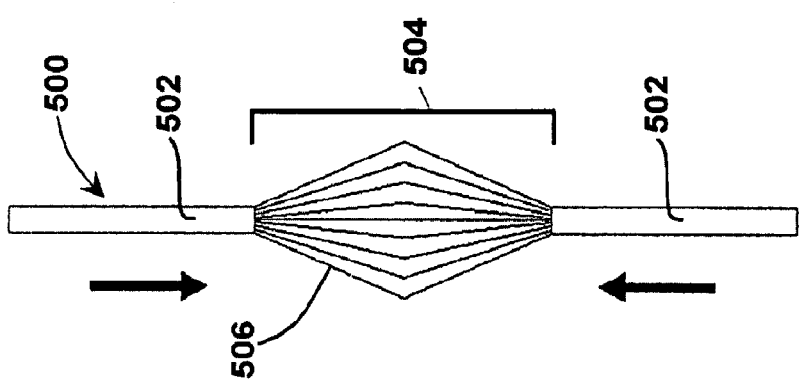
FIG. 5B shows a drill of an umbrella device according to at least one embodiment of the present application with moving shaft portions, as described herein.
Figure 5A:
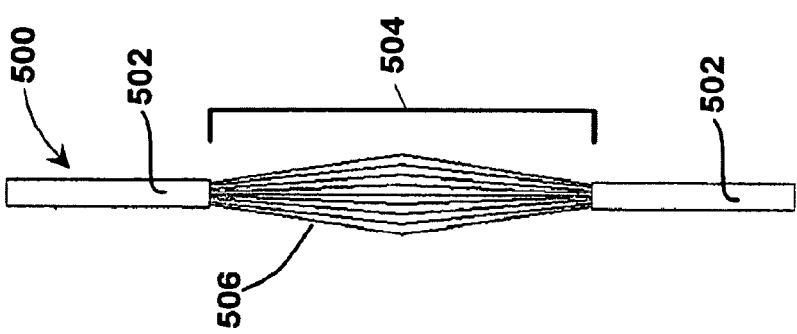
FIG. 5A shows a drill of an umbrella device according to at least one embodiment of the present application, as described herein.

An exemplary drill of an umbrella device of the present disclosure is shown in FIGS. 5A-5C. As shown in FIGS. 5A-5C, drill 500 comprises shaft portions 502 and a cutting portion 504. Cutting portion 504 may comprise, for example, one or more blades 506 operable to grind, for example, a calcified aortic valve. FIG. 5A shows an exemplary embodiment of drill 500 in a native (non-operational) state. FIG. 5B shows drill 500 in action, noting that, in this exemplary embodiment, as drill 500 operates, shaft portions 502 move in the direction of the arrows as shown in FIG. 5B, allowing the overall diameter of cutting portion 504 to increase. FIG. 5C shows an embodiment of drill 500 in full operation, noting that shaft portions 502 may move toward one another as noted by the straight arrows, while cutting portion 504 rotates about an axis provided by shaft portions as shown by the curved arrow. Rotation of cutting portion 504 may generate a force to grind calcified aortic valve as described herein. It can be appreciated that drill 500, as shown in FIGS. 5A-5C, is only one of several drills known or anticipated in the art may that be useful with the disclosure of the present application.

Figure 6:
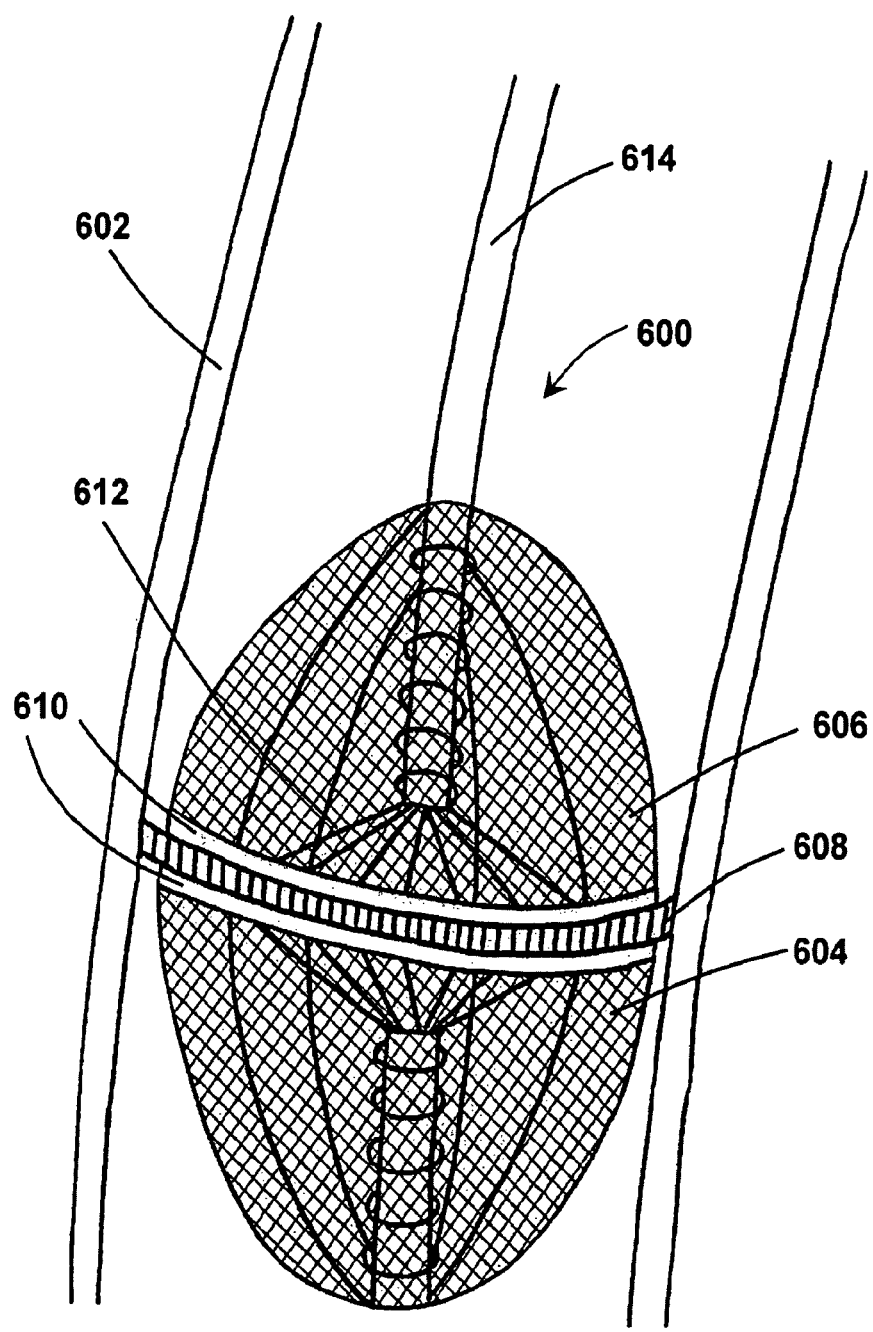
FIG. 6 shows an umbrella device according to at least one embodiment of the present application surrounding a calcified aortic valve, as described herein.

An exemplary embodiment of an umbrella device positioned within a vessel at or near a calcified aortic valve is shown in FIG. 6. As shown in FIG. 6, umbrella device 600 is positioned within vessel 602, with first umbrella 604 and second umbrella 606 deployed and engaging calcified aortic valve 608. In at least one embodiment, umbrella device 600 may be operable to cauterize calcified aortic valve 608 using cauterizing mechanisms 610 positioned about the circumferential outer edges of first umbrella 604 and second umbrella 606. Operation of cauterizing mechanisms 610, for example, would cauterize calcified aortic valve 608 about its circumference at or near the boundary provided by vessel 602. Cauterization of calcified aortic valve 608 allows calcified aortic valve 608 to detach from vessel 602 and remain within the space defined by the outer perimeters of first umbrella 604 and second umbrella 606. After cauterization, drill 612 may be operated to grind (or chop) cauterized calcified aortic valve 608 into small pieces.

In at least one embodiment of operating umbrella device 600 as described herein, drill 612 would grind cauterized calcified aortic valve 608 into pieces small enough to allow for the eventual collapsing of first umbrella 604 and second umbrella 606 while keeping most or all of the ground calcified aortic valve 608 within the space defined by collapsed first umbrella 604 and second umbrella 606. It can be appreciated that the mesh used for first umbrella 604 and second umbrella 606 may be of varying mesh sizes for a particular application, noting that a mesh having an aperture size smaller than the ground pieces of calcified aortic valve 608 is optimal.

In at least one embodiment, first umbrella 604 and second umbrella 606 may comprise magnetic material so that first umbrella 604 and second umbrella 606 may be magnetically attracted to shaft 614. In such an embodiment, first umbrella 604 and second umbrella 606 may collapse inwards to shaft 614, exerting an inward force to further crush the calcified debris and close first umbrella 604 and second umbrella 606.

Figure 7:
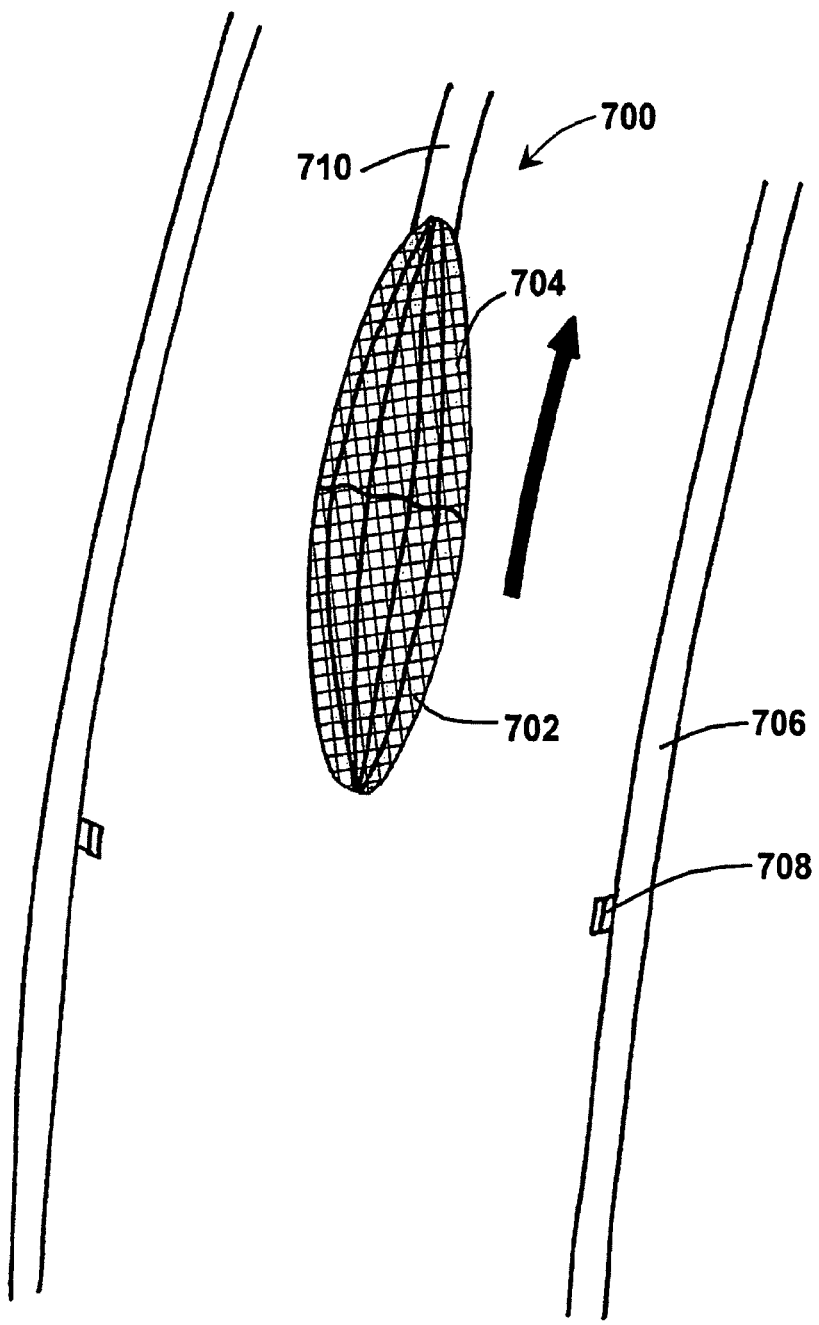
FIG. 7 shows an umbrella device according to at least one embodiment of the present application with a ground calcified aortic valve present therein, as described herein.

FIG. 7 shows an embodiment of an umbrella device being removed from a vessel after cauterization and grinding of calcified aortic valve. As shown in FIG. 7, umbrella device 700 comprises collapsed first umbrella 702 and second umbrella 704, whereby the collapsed circumferential edges of first umbrella 702 and second umbrella 704 have engaged one another to form a capsule therein. Cauterized and ground calcified aortic valve present within the space defined by first umbrella 702 and second umbrella 704 may then be removed from vessel 706 in the direction of the arrow shown in FIG. 7. It can be appreciated that if the apertures within the mesh comprising first umbrella 702 and second umbrella 704 are smaller than the ground calcified aortic valve particles, said particles will remain enclosed within the chamber defined by first umbrella 702 and second umbrella 704, protecting against potential embolization of calcified debris during such aortic valve resection. It can be further appreciated that an optional suction system as known in the art, comprising a suction catheter and a suction source, for example, may be useful for the intentional removal of said calcified debris in the vicinity of the original calcified aortic valve.

As shown in FIG. 7, umbrella device 700 removed the majority of calcified aortic valve, leaving a ring remnant 708 of calcified aortic valve. Allowing a ring remnant 708 to remain may provide for additional vessel 706 support to protect the aortic wall. Furthermore, collapsed first umbrella 702 and second umbrella 704 may optionally be retracted within the lumen of shaft catheter 710 to facilitate removal of umbrella device 700 from vessel 706.

Figure 8A:
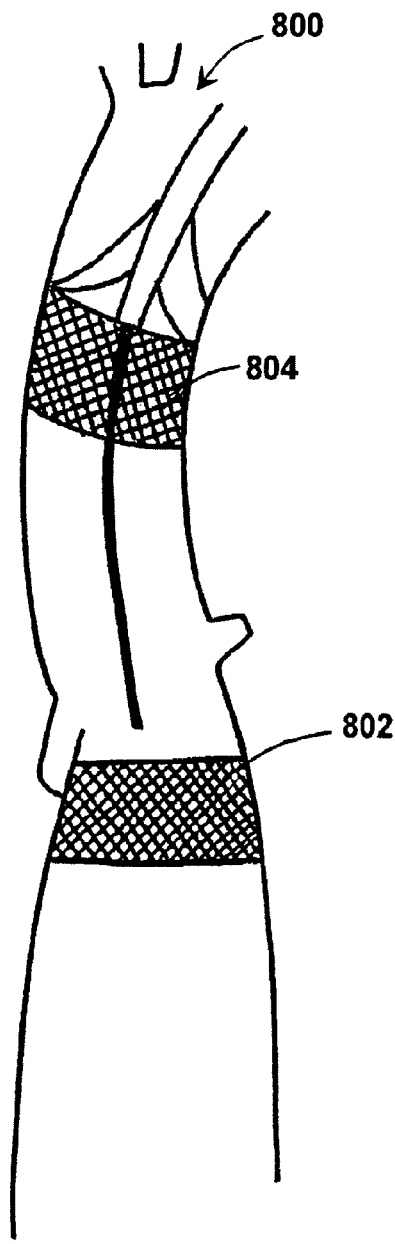
FIG. 8A shows an umbrella device according to at least one embodiment of the present application useful for positioning a permanent stent valve, as described herein.
Figure 8B:
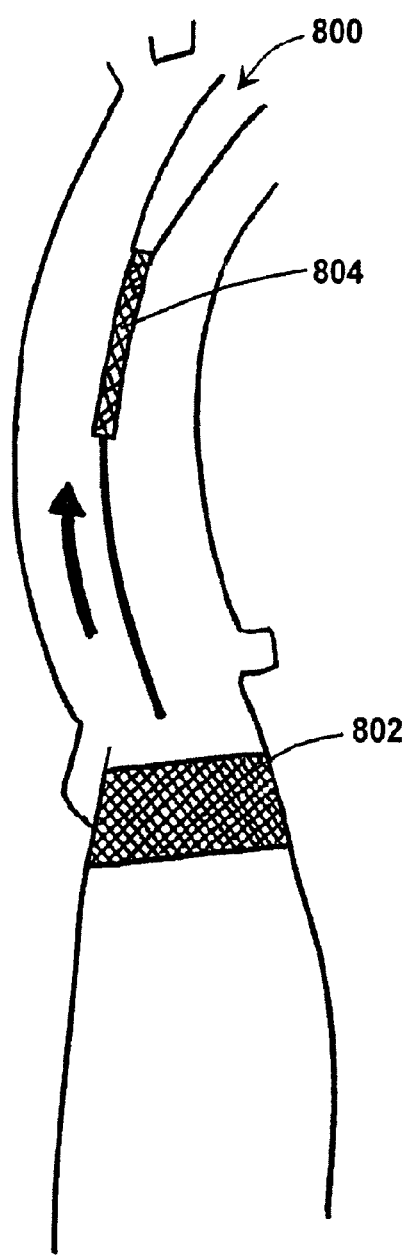
FIG. 8B shows an umbrella device according to at least one embodiment of the present application useful for removing a temporary stent valve, as described herein.

FIGS. 8A and 8B show exemplary embodiments of an umbrella device useful for removing temporary stent valve and placing a permanent stent valve. As shown in FIG. 8A, umbrella device 800 may be used to position permanent stent valve 802 at or near the site of the previously-removed calcified aortic valve. When positioned, the portion of umbrella device 800 useful for positioning permanent stent valve 802 may be withdrawn as shown in FIG. 8B, and temporary stent valve 804 may then be collapsed and removed in the direction of the arrow shown in FIG. 8B. It can be appreciated that in at least one embodiment of the present disclosure, umbrella device 800 may be useful for the excision of a valve as described herein, but a second apparatus, for example a catheter with a wire, may be useful for the placement of permanent stent valve 802.

Figure 9B:
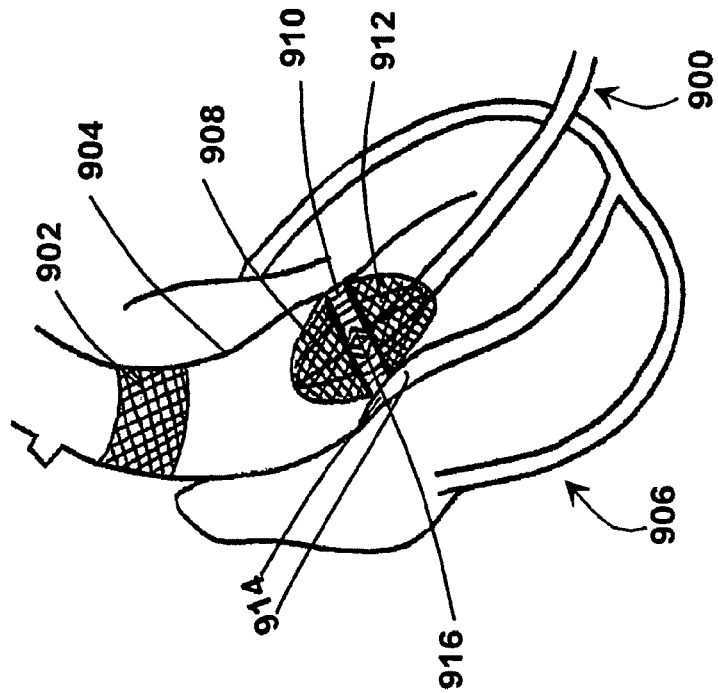
FIG. 9B shows an umbrella device according to at least one embodiment of the present application with the second umbrella positioned at an aortic valve site within a vessel, as described herein.
Figure 9A:
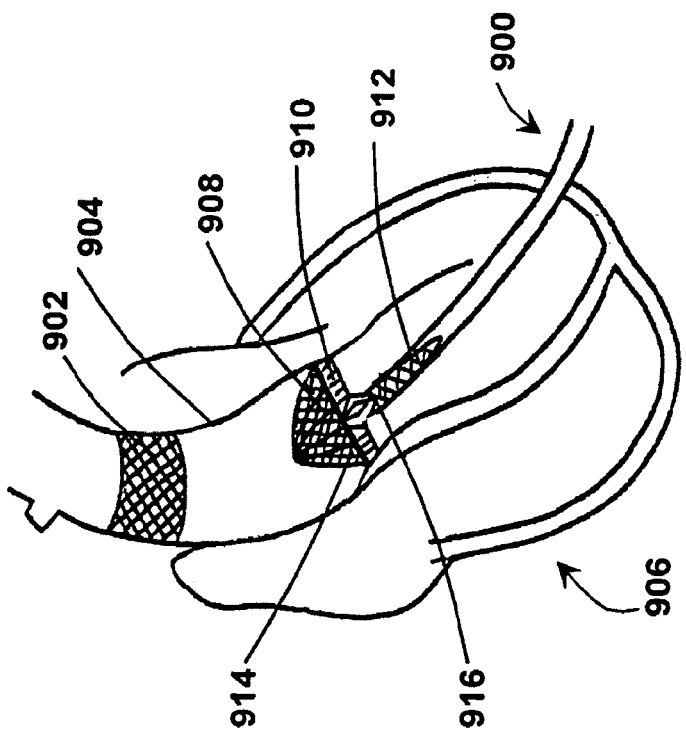
FIG. 9A shows an umbrella device according to at least one embodiment of the present application with the first umbrella positioned at an aortic valve site within a vessel, as described herein.

FIGS. 9A and 9B show exemplary embodiments of an umbrella device positioned within a heart via the apex of the heart mini-invasively rather than percutaneously as described herein. As shown in FIG. 9A, umbrella device 900 positioned a temporary stent valve 902 within a vessel 904 of a heart 906. When temporary stent valve 902 is positioned, first umbrella 908 may be deployed as described herein to engage one side of calcified aortic valve 910. As shown in FIG. 9B, second umbrella 912 may also be deployed as described herein to engage both sides of calcified aortic valve 910. Upon deployment of first umbrella 908 and second umbrella 912, cauterizing mechanism 914 present on either or both of the circumferential edges of first umbrella 908 and/or second umbrella 912 may be operated to cauterize calcified aortic valve 910, whereby drill 916 may be operated to grind calcified aortic valve 910 as described herein.

Figure 10A:
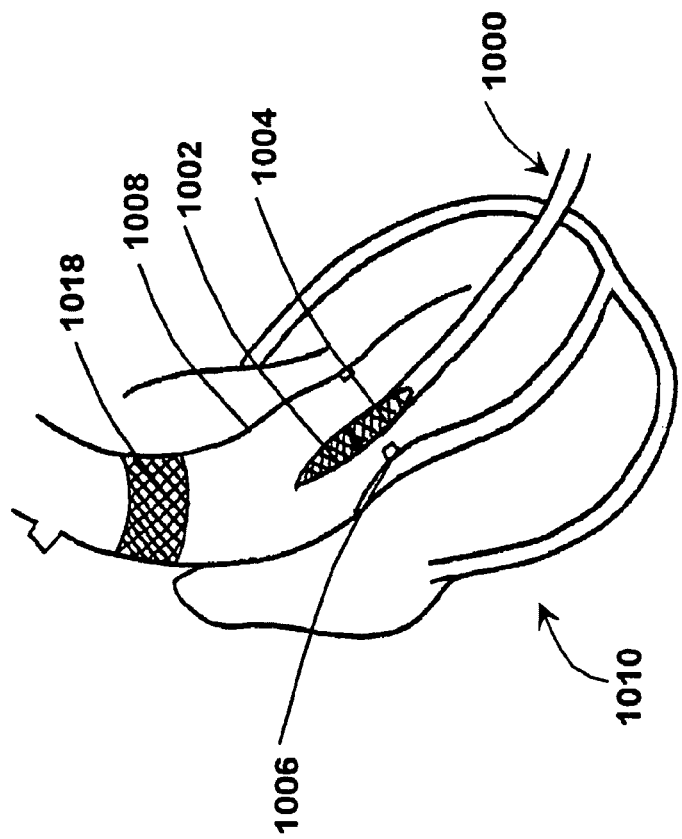
FIG. 10A shows an umbrella device according to at least one embodiment of the present application with a ground calcified aortic valve present therein, as described herein.

FIG. 10A shows an embodiment of an umbrella device with collapsed umbrellas to remove the ground calcified aortic valve. As shown in FIG. 10A, umbrella device 1000 comprises collapsed first umbrella 1002 and collapsed second umbrella 1004, with ground calcified aortic valve contained therein. In this exemplary procedure, portions of calcified aortic valve 1006 remain adhered to vessel 1008 of heart 1010 to allow for vessel 1008 wall support.

FIG. 10B shows an embodiment of an umbrella device useful for placing a permanent stent valve. As shown in FIG. 10B, permanent stent valve 1012 has been placed within vessel 1008 of heart 1010, using, for example, shaft catheter 1014 or wire 1016 positioned therethrough. As shown in FIG. 10B, after permanent stent valve 1012 has been positioned, temporary stent valve 1018 (shown in FIG. 10A) may be removed.

As described herein, umbrella device may be useful percutaneously during a procedure performed under total or local anesthesia with conscious sedation of the patient. The procedure itself may be visualized using fluoroscopy and a transesophageal echo.

In at least one exemplary procedural method, a femoral arterial or iliac puncture is used to insert the umbrella device to the left ventricle cavity. As described above with respect to FIGS. 2A and 2B, a temporary stent valve may be inserted in the ascending aorta at the beginning of the procedure to avoid a massive aortic insufficiency during valve resection.

Umbrella device may be advanced over a guide wire through the temporary stent valve to reach the calcified aortic valve, passing through the stenotic orifice into the left ventricle. The first umbrella of the umbrella device may then be deployed on the inferior/ventricular side of the calcified aortic valve and fitted around the valve to separate the mitral valve leaflets as shown in FIGS. 3A and 3B. The second umbrella of the umbrella device may then be deployed on the superior/atrial side of the calcified aortic valve, with the drill being positioned at the level of the aortic valve orifice, as shown in FIGS. 4A and 4B.

When the first umbrella and second umbrella have engaged the calcified aortic valve (as shown in FIGS. 4B and 6), a cauterizing mechanism may be used to cauterize the calcified aortic valve to allow for subsequent grinding by the drill as described herein. After the valve has been cauterized and ground, the first umbrella and second umbrella may collapse to facilitate removal of the ground valve contained within the capsule formed by the first umbrella and the second umbrella. The umbrella device, as referenced herein, may also be retracted within the shaft catheter to facilitate removal of the umbrella device from, for example, the aorta to the iliac or femoral artery and finally out of the patient's body as shown in FIG. 7.

The aforementioned exemplary procedure may be performed under a beating heart off pump or a beating heart with, for example, femo-femoral extracorporeal pump support. After removal of the native aortic valve and the permanent stent valve has been positioned as shown in FIG. 8A, the temporary stent valve may be removed as shown in FIG. 8B.

While various embodiments of devices, systems, and methods for percutaneous valve removal have been described in considerable detail herein, the embodiments are merely offered by way of non-limiting examples of the disclosure described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

The invention claimed is:

1. An umbrella device for removing a valve the umbrella device comprising:
   an elongated shaft having a distal end;
   a first umbrella comprising a first mesh, the first umbrella coupled to the shaft at or near the distal end of the shaft;
   a second umbrella comprising a second mesh, the second umbrella coupled to the shaft proximal to the first umbrella; and
   a mechanical drill rotatably coupled to the shaft and positioned between the first umbrella and the second umbrella; and
   at least one electrical coil positioned along portions of the shaft at or near the first umbrella and the second umbrella, wherein the at least one electrical coil is/are independently operable to generate a magnetic force upon introduction of a current to said at least one electrical coil.

2. The umbrella device of claim 1, wherein the shaft further comprises a wall defining a lumen therethrough.

3. The umbrella device of claim 2, further comprising a wire positioned within at least part of the lumen of the shaft, the wire operable to position a stent valve within a vessel.

4. The umbrella device of claim 1, wherein the first umbrella and the second umbrella are capable of mechanical expansion and contraction.

5. The umbrella device of claim 1, wherein the current is introduced from a current source, the current source operably coupled to each of the at least one electrical coil.

6. The umbrella device of claim 1, wherein the first mesh and the second mesh define mesh apertures having an opening large enough to allow blood to pass therethrough but small enough to prevent ground valve from passing therethrough.

7. The umbrella device of claim 1, wherein the first mesh and the second mesh define mesh apertures having their largest cross-dimension no larger than about 100 μm in diameter.

8. The umbrella device of claim 1, wherein the first mesh and the second mesh comprise mesh material selected from the group consisting of stainless steel, microexpandable metal, polytetrafluoroethylene coated stainless steel, and polyethylene terephthalate coated stainless steel.

9. The umbrella device of claim 1, wherein the second umbrella comprises a cauterizing mechanism coupled to a circumferential edge of the second umbrella, wherein the cauterizing mechanism comprises a cauterizing wire capable of increasing in temperature from the introduction of a current to said cauterizing wire.

10. The umbrella device of claim 1, further comprising an electrical source coupled to the mechanical drill, the electrical source operable to start and stop operation of the mechanical drill.

11. The umbrella device of claim 1, wherein the mechanical drill is operable via operation of a suction source coupled thereto, the suction source operable to start and stop the mechanical drill.

12. The umbrella device of claim 1, wherein the umbrella device is operable to be introduced into a vessel, engage a valve, and remove said valve.

13. The umbrella device of claim 1, forming part of a system for removing a valve from a vessel, the system further comprising:
at least one mechanism capable of expanding and contracting the first umbrella and the second umbrella.

14. The umbrella device of claim 13, wherein the at least one mechanism comprises at least one rib slidingly coupled to the shaft, wherein the at least one rib may be moved along the shaft toward the distal end and toward the proximal end to mechanically expand and contract the first umbrella and the second umbrella.

15. The umbrella device of claim 13, wherein the at least one mechanism comprises at least one electromechanical mechanism operable to electromechanically expand and contract the first umbrella and the second umbrella.

16. An umbrella device for removing a valve the umbrella device comprising:
an elongated shaft having a distal end;
a first umbrella comprising a first mesh, the first umbrella coupled to the shaft at or near the distal end of the shaft;
a second umbrella comprising a second mesh, the second umbrella coupled to the shaft proximal to the first umbrella; and
a mechanical drill rotatably coupled to the shaft and positioned between the first umbrella and the second umbrella;
wherein at least one of the first umbrella and/or the second umbrella comprises a cauterizing mechanism coupled to a circumferential edge of the first umbrella and/or the second umbrella, wherein the cauterizing mechanism comprises a cauterizing wire capable of increasing in temperature from the introduction of a current to said cauterizing wire.

17. The umbrella device of claim 16, wherein the shaft further comprises a wall defining a lumen therethrough, and wherein the device further comprises a wire positioned within at least part of the lumen of the shaft, the wire operable to position a stent valve within a vessel.

18. A method for removing a valve from a vessel, the method comprising the step of:
operating an umbrella device to remove a valve within a vessel, the umbrella device comprising:
an elongated shaft having a distal end;
a first umbrella comprising a first mesh, the first umbrella coupled to the shaft at or near the distal end of the shaft;
a second umbrella comprising a second mesh, the second umbrella coupled to the shaft proximal to the first umbrella; and
a mechanical drill rotatably coupled to the shaft and positioned between the first umbrella and the second umbrella;
wherein at least one of the first umbrella and/or the second umbrella comprises a cauterizing mechanism coupled to a circumferential edge of the first umbrella and/or the second umbrella, wherein the cauterizing mechanism comprises a cauterizing wire capable of increasing in temperature from the introduction of a current to said cauterizing wire; and
operating the cauterizing mechanism to cauterize the valve.

19. The method of claim 18, wherein the step of operating comprises the steps of:
deploying the first umbrella on a first side of the valve;
deploying the second umbrella on a second side of the valve; and
operating the mechanical drill to grind the valve.

20. The method of claim 19, further comprising the steps of:
collapsing the first umbrella and the second umbrella; and
withdrawing the umbrella device from the vessel.

* * * * *